(12) United States Patent
Kimba

(10) Patent No.: US 8,687,197 B2
(45) Date of Patent: Apr. 1, 2014

(54) METHOD OF MONITORING PROGRESS OF SUBSTRATE POLISHING AND POLISHING APPARATUS

(75) Inventor: Toshifumi Kimba, Tokyo (JP)

(73) Assignee: Ebara Corporation, Tokyo (JP)

( * ) Notice: Subject to any disclaimer, the term of this patent is extended or adjusted under 35 U.S.C. 154(b) by 464 days.

(21) Appl. No.: 13/183,555

(22) Filed: Jul. 15, 2011

(65) Prior Publication Data

US 2012/0019830 A1 Jan. 26, 2012

(30) Foreign Application Priority Data

Jul. 23, 2010 (JP) ................................. 2010-165782

(51) Int. Cl.
*G01N 21/55* (2006.01)
*H01L 21/66* (2006.01)
*B24B 49/12* (2006.01)
*B24B 37/013* (2012.01)

(52) U.S. Cl.
CPC ............... *H01L 22/12* (2013.01); *G01N 21/55* (2013.01); *B24B 49/12* (2013.01); *B24B 37/013* (2013.01)
USPC .................... 356/448; 356/445; 451/5; 451/6

(58) Field of Classification Search
None
See application file for complete search history.

(56) References Cited

U.S. PATENT DOCUMENTS

| 5,486,129 | A | * | 1/1996 | Sandhu et al. ..................... 451/6 |
| 6,590,645 | B1 | * | 7/2003 | Chen et al. ................. 356/237.2 |
| 7,252,575 | B2 | | 8/2007 | Kobayashi et al. |
| 2005/0179910 | A1 | * | 8/2005 | Bartov ........................... 356/503 |
| 2008/0243433 | A1 | * | 10/2008 | Ravid et al. ..................... 702/170 |
| 2010/0093260 | A1 | | 4/2010 | Kobayashi et al. |
| 2010/0130100 | A1 | * | 5/2010 | David et al. ....................... 451/6 |

FOREIGN PATENT DOCUMENTS

| JP | 2003-042721 | 2/2003 |
| JP | 2004-154928 | 6/2004 |
| WO | 2007/024807 | 3/2007 |
| WO | 2008/103964 | 8/2008 |

* cited by examiner

*Primary Examiner* — Gregory J Toatley
*Assistant Examiner* — Juan D Valentin, II
(74) *Attorney, Agent, or Firm* — Wenderoth, Lind & Ponack, L.L.P.

(57) ABSTRACT

A method of monitoring progress of polishing of a substrate having at least two regions including a first region and a second region with different structures is provided. The method includes: applying light to plural measurement points on the substrate during polishing of the substrate; receiving reflected light from each measurement point; measuring intensity of the reflected light; producing a spectrum of the reflected light from the intensity; classifying the spectrum as spectrum of the reflected light from the first region or as spectrum of the reflected light from the second region based on a shape of the spectrum or the intensity of the reflected light; and monitoring progress of polishing of the substrate based on a temporal change in the spectrum of the reflected light from the first region.

23 Claims, 11 Drawing Sheets

METHOD OF MONITORING PROGRESS OF SUBSTRATE POLISHING AND POLISHING APPARATUS

BACKGROUND OF THE INVENTION

1. Field of the Invention

The present invention relates to a method of monitoring progress of polishing of a substrate (e.g., a semiconductor wafer) and a polishing apparatus for a substrate. More particularly, the present invention relates to a method of monitoring the progress of substrate polishing and determining a polishing end point based on a change in spectrum obtained from reflected light from the substrate.

2. Description of the Related Art

In fabrication processes of a semiconductor device, several kinds of materials are repeatedly deposited in the form of film on a silicon wafer to form a multilayer structure. It is important for forming such a multilayer structure to planarize a surface of a top layer. Chemical mechanical polishing (CMP) is widely used as one solution for achieving such planarization.

The chemical mechanical polishing (CMP) is performed by a polishing apparatus. The polishing apparatus of this type typically includes a polishing table supporting a polishing pad thereon, a top ring for holding a substrate (a wafer with a film formed thereon), and a polishing liquid supply mechanism for supplying a polishing liquid onto the polishing pad. Polishing of a substrate is performed as follows. The top ring presses a surface of the substrate against the polishing pad, while the polishing liquid supply mechanism supplies the polishing liquid onto the polishing pad. In this state, the top ring and the polishing table are rotated to provide relative movement between the substrate and the polishing pad, thereby polishing the film that forms the surface of the substrate.

Generally, the polishing apparatus has a polishing end point detection device. An optical polishing end point detection device is one example of such a polishing end point detection device. This device is configured to direct light to the surface of the substrate and to determine a polishing end point based on spectrum of the light reflected from the substrate. For example, a Japanese laid-open patent publication No. 2004-154928 discloses a method in which intensity of the reflected light is processed in order to remove noise components to create characteristic value and the polishing end point is determined based on a distinctive point (i.e., a local maximum point or local minimum point) of temporal variation in the characteristic value.

The spectrum is an arrangement of the light intensity in the order of wavelength, and indicates the light intensity at each wavelength. The characteristic value created from the spectrum varies periodically with polishing time, and the local maximum point and the local minimum point appear alternately, as shown in FIG. 1. This phenomenon is due to interference between light waves. Specifically, the light, directed to the substrate, is reflected off an interface between a medium and the film and an interface between the film and a layer beneath the film. The light waves reflected from these interfaces interfere with each other. The manner of interference between the light waves varies depending on the thickness of the film (i.e., a length of an optical path). Therefore, the intensity of the reflected light from the substrate varies periodically in accordance with the thickness of the film.

The above-described optical polishing end point detection device counts the number of distinctive points (i.e., the local maximum points or local minimum points) of the temporal variation in the characteristic value during polishing and monitors the polishing progress based on the number of distinctive points. The polishing process is terminated when a predetermined period of time has elapsed from a point of time when the number of distinctive points has reached a predetermined value.

There has recently been developed a top ring capable of pressing multiple zones of the substrate independently by using multiple pressing mechanisms (e.g., air bags). This type of top ring can adjust pressing forces on the zones (e.g., a central zone, an intermediate zone, an edge zone) based on a polishing profile (i.e., a cross-sectional shape of the film) of the substrate during polishing. In order to monitor the progress of polishing in each zone of the substrate, it is necessary to direct the light to the substrate during polishing and to obtain the reflected light from each zone of the substrate. Specifically, a light source, which is embedded in the polishing tale, illuminates a plurality of measurement points on the surface of the substrate, and a light receiver, which is adjacent to the light source, receives reflected light from the substrate.

In order to obtain an accurate polishing profile of the substrate, it is desirable to apply the light to a number of measurement points (e.g., 100 measurement points) on the substrate and to receive the reflected light from each of the measurement points. However, since various regions with different structures exist on the substrate surface, the spectrum that is produced from the reflected light can vary greatly depending on region. As a result, film-thickness information obtained for each measurement point may vary greatly, and an accurate polishing profile cannot be obtained.

For example, a flash memory is a device having regular surface structures and irregular surface structures. FIG. 2A is a view of a substrate having plural flash memories formed on a surface thereof. Flash memories 4 formed on a substrate W are cut off one by one along dicing lines 7. As shown in FIG. 2B, each flash memory 4 typically has two cell regions 5 and a peripheral region 6 surrounding the cell regions 5.

The cell region 5 is a cell array having memory cells in a matrix arrangement and has regular structures. In such cell region 5, the spectrum that is created from the reflected light varies according to the progress of polishing. In contrast, the peripheral region 6 is a region in which interconnects extend randomly, and structure thereof differs from area to area. In such peripheral region 6, the spectrum that is created from the reflected light can vary depending on area to which the light is applied. Further, as shown in FIG. 2A, there are the dicing lines 7 around the peripheral region 6. The presence of the dicing lines 7 may result in the creation of spectrum that differs from spectra obtained in the cell region 5 and the peripheral region 6. However, since the dicing lines 7 are small areas as compared with the peripheral region 6, in the following descriptions the peripheral region 6 is defined to include the dicing lines 7.

The spectrum of the reflected light from the cell region 5 and the spectrum of the reflected light from the peripheral region 6 vary greatly due to difference in their structures. This causes problems for accurate monitoring of the progress of polishing and accurate detection of the polishing end point.

SUMMARY OF THE INVENTION

The present invention has been made in view of the above drawbacks. It is therefore an object of the present invention to provide a method and a polishing apparatus capable of monitoring the progress of substrate polishing accurately.

One aspect of the present invention for achieving the above object is to provide a method of monitoring progress of polishing of a substrate having on a surface thereof at least two regions including a first region and a second region with different structures. The method includes: polishing the substrate by pressing the substrate against a polishing pad on a rotating polishing table; during the polishing of the substrate, applying light to plural measurement points on the substrate; receiving reflected light from each measurement point; measuring intensity of the reflected light throughout a predetermined wavelength range; producing a spectrum of the reflected light from measurement values of the intensity; classifying the spectrum as spectrum of the reflected light from the first region or as spectrum of the reflected light from the second region based on a shape of the spectrum or the intensity of the reflected light; and monitoring the progress of polishing of the substrate based on a temporal change in the spectrum of the reflected light from the first region.

In a preferred aspect of the present invention, the method includes further monitoring the progress of polishing of the substrate based on a temporal change in the spectrum of the reflected light from the second region.

In a preferred aspect of the present invention, the monitoring of the progress of polishing of the substrate based on the temporal change in the spectrum of the reflected light from the first region and the monitoring of the progress of polishing of the substrate based on the temporal change in the spectrum of the reflected light from the second region are performed simultaneously or successively.

In a preferred aspect of the present invention, the monitoring of the progress of polishing of the substrate based on the temporal change in the spectrum of the reflected light from the first region and the monitoring of the progress of polishing of the substrate based on the temporal change in the spectrum of the reflected light from the second region are performed according to different polishing monitoring algorithms.

In a preferred aspect of the present invention, the monitoring of the progress of polishing of the substrate is performed according to at least two polishing monitoring algorithms, which are switched from one to another during polishing.

In a preferred aspect of the present invention, the classifying of the spectrum includes: calculating a square-sum of difference between the spectrum and a reference spectrum selected from plural reference spectra each associated with a film thickness; repeating the calculating of the square-sum to obtain plural square-sums corresponding to the plural reference spectra; determining a reference spectrum corresponding to a smallest of the plural square-sums to obtain a film thickness associated with the determined reference spectrum; classifying the spectrum as a spectrum of the reflected light from the first region when the film thickness obtained is within a predetermined reference range; and classifying the spectrum as a spectrum of the reflected light from the second region when the film thickness obtained is not within the predetermined reference range.

In a preferred aspect of the present invention, the classifying of the spectrum includes: classifying the spectrum as a spectrum of the reflected light from the first region when the number of local maximum points and/or local minimum points that appear on the spectrum agrees with a predetermined reference number; and classifying the spectrum as a spectrum of the reflected light from the second region when the number of local maximum points and/or local minimum points that appear on the spectrum does not agree with the predetermined reference number.

In a preferred aspect of the present invention, the classifying of the spectrum includes: decomposing the spectrum into frequency components by fast Fourier transform; classifying the spectrum as a spectrum of the reflected light from the first region when the frequency components substantially agree with predetermined reference frequency components; and classifying the spectrum as a spectrum of the reflected light from the second region when the frequency components do not substantially agree with the predetermined reference frequency components.

In a preferred aspect of the present invention, the classifying of the spectrum includes: comparing the intensity of the reflected light with a predetermined threshold value; classifying the spectrum as a spectrum of the reflected light from the first region when the intensity of the reflected light is not less than the predetermined threshold value; and classifying the spectrum as a spectrum of the reflected light from the second region when the intensity of the reflected light is less than the predetermined threshold value.

In a preferred aspect of the present invention, the method further includes: determining a polishing end point of the substrate based on the temporal change in the spectrum of the reflected light from the first region.

In a preferred aspect of the present invention, the substrate has memories formed on the surface thereof; the first region is a cell region of each memory; and the second region is a peripheral region surrounding the cell region.

In a preferred aspect of the present invention, the first region has regular structures and the second region has irregular structures.

Another aspect of the present invention is to provide an apparatus for polishing a substrate having on a surface thereof at least two regions including a first region and a second region with different structures. The apparatus includes: a rotatable polishing table for supporting a polishing pad thereon; a top ring configured to press the substrate against the polishing pad; a light-applying unit configured to apply light to plural measurement points on the substrate; a light-receiving unit configured to receive reflected light from each measurement point; a spectroscope configured to measure intensity of the reflected light throughout a predetermined wavelength range; and a processing device configured to produce a spectrum of the reflected light from measurement values of the intensity. The processing device is configured to classify the spectrum as spectrum of the reflected light from the first region or as spectrum of the reflected light from the second region based on a shape of the spectrum or the intensity of the reflected light, and monitor the progress of polishing of the substrate based on a temporal change in the spectrum of the reflected light from the first region.

According to the present invention, the spectrum is classified based on optical information that varies depending on surface structure of the substrate. Therefore, the progress of polishing can be monitored based only on the spectrum suitable for monitoring of polishing. Further, a polishing end point can be determined. As a result, accurate monitoring of the progress of substrate polishing and accurate detection of the polishing end point can be realized.

DETAILED DESCRIPTION OF THE PREFERRED EMBODIMENTS

Figure 3A:
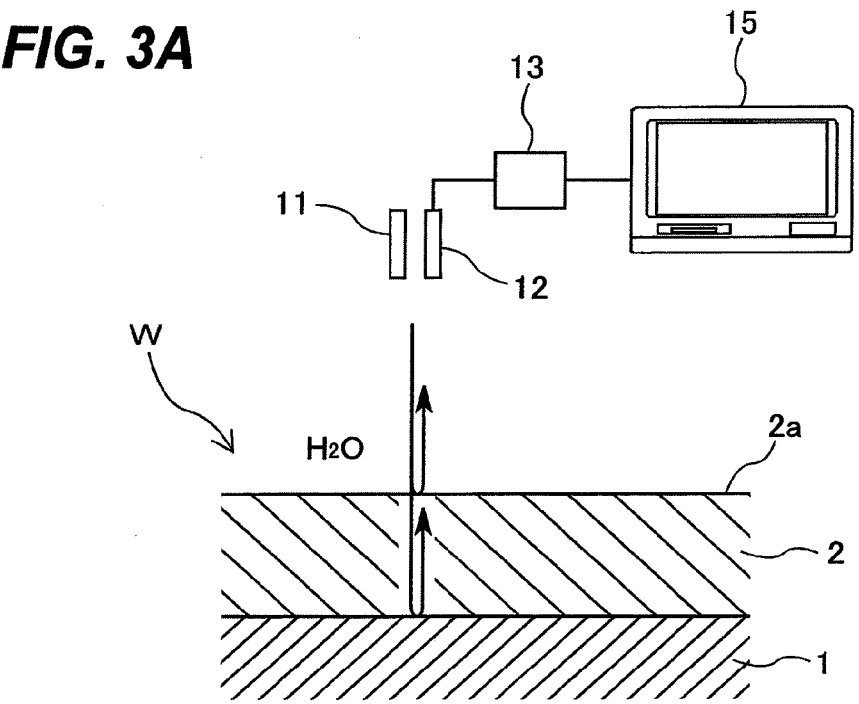
FIG. 3A is a schematic view illustrating the principle of a polishing monitoring method according to an embodiment of the present invention.
Figure 3B:
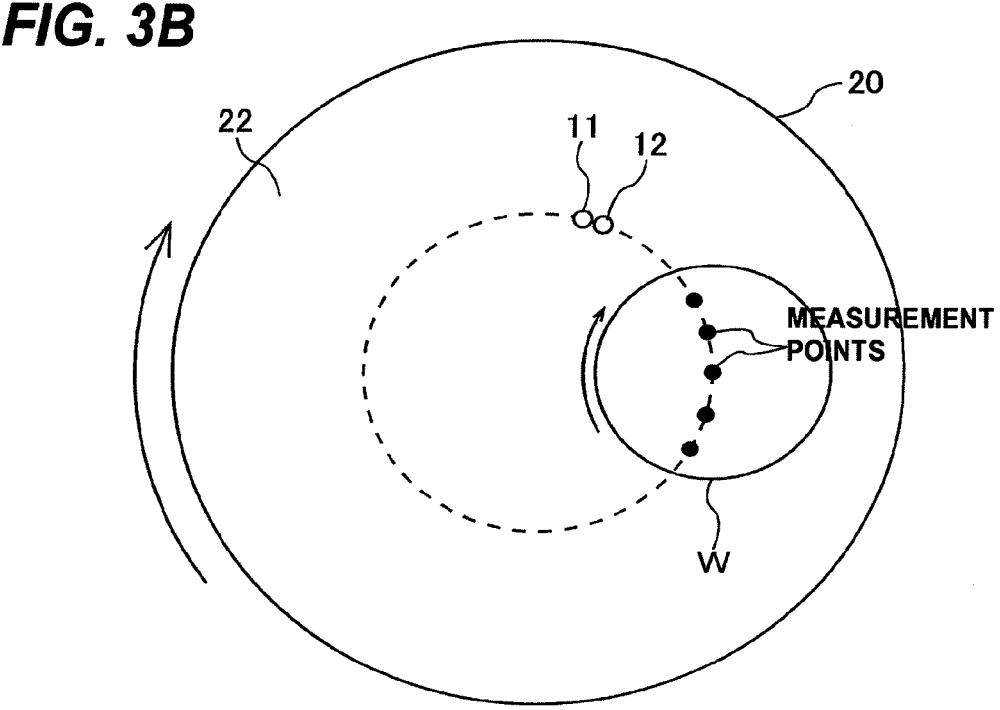
FIG. 3B is a plan view showing positional relationship between a substrate and a polishing table.

Embodiments of the present invention will be described below with reference to the drawings. FIG. 3A is a schematic view showing the principle of a polishing monitoring method according to an embodiment of the present invention, and FIG. 3B is a plan view showing a positional relationship between a substrate and a polishing table. As shown in FIG. 3A, a substrate W, to be polished, has an underlying layer 1 (e.g., a silicon layer) and a film 2 (e.g., a dielectric film, such as $SiO_2$, having a light permeability) formed on the underlying layer 1. A surface 2a of the substrate W is pressed against a polishing pad 22 on a rotating polishing table 20. The surface 2a of the substrate W is thus polished by sliding contact with the polishing pad 22. During polishing of the substrate W, a polishing liquid (slurry) is supplied onto the polishing pad 22.

A light-applying unit 11 and a light-receiving unit 12 are arranged so as to face the surface of the substrate W. The light-applying unit 11 is configured to emit light in a direction substantially perpendicular to the surface of the substrate W, and the light-receiving unit 12 is configured to receive the reflected light from the substrate W. The light emitted by the light-applying unit 11 is visible light. In order not to allow the polishing liquid to enter a path of the light, flow of pure water is formed in a space between the light-applying unit 11 and light-receiving unit 12 and the substrate W.

As shown in FIG. 3B, the light is applied to plural regions including the center of the substrate W each time the polishing table 20 makes one revolution. A spectroscope 13 is coupled to the light-receiving unit 12. This spectroscope 13 decomposes the reflected light according to wavelength and measures the intensity of the reflected light over a predetermined wavelength range. The wavelength range that can be measured by the spectroscope 13 is, for example, from 400 nm to 800 nm.

A processing device 15 is coupled to the spectroscope 13. This processing device 15 is configured to read measurement data obtained by the spectroscope 13 and to produce intensity distribution of the reflected light from the measured values of the intensity. More specifically, the processing device 15 produces a spectrum which indicates the light intensity at each wavelength. This spectrum can be expressed as a line graph indicating a relationship between wavelength and intensity of the reflected light. The processing device 15 is further configured to monitor the progress of polishing and to determine a polishing end point from a change in the spectrum. A general-purpose computer or a dedicated computer can be used as the processing device 15. The processing device 15 performs predetermined processing steps according to a program (or computer software).

Figure 2A:
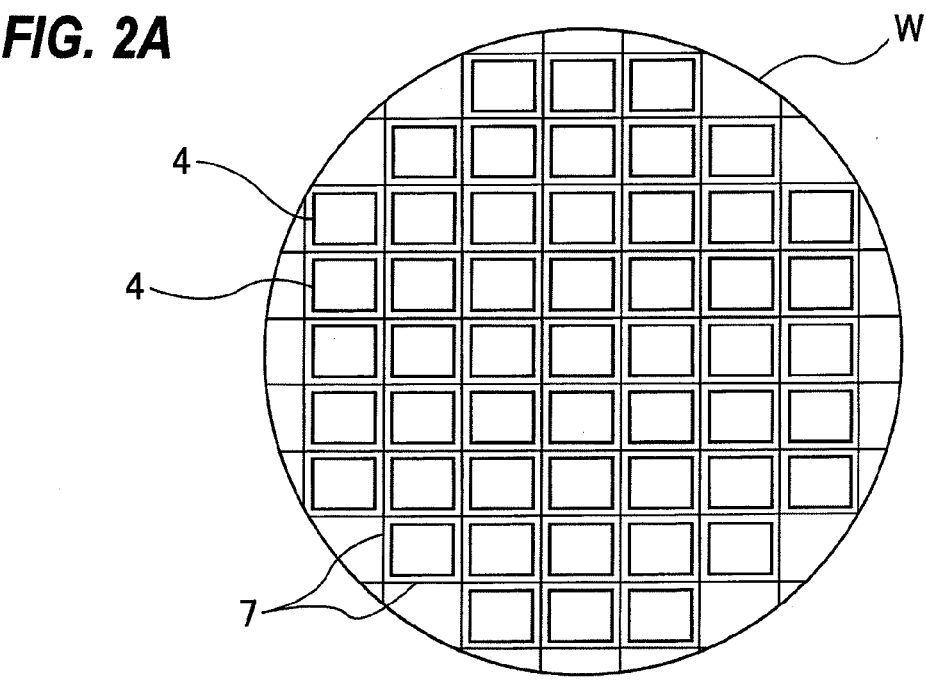
FIG. 2A is a view showing a substrate having flash memories formed thereon.
Figure 2B:
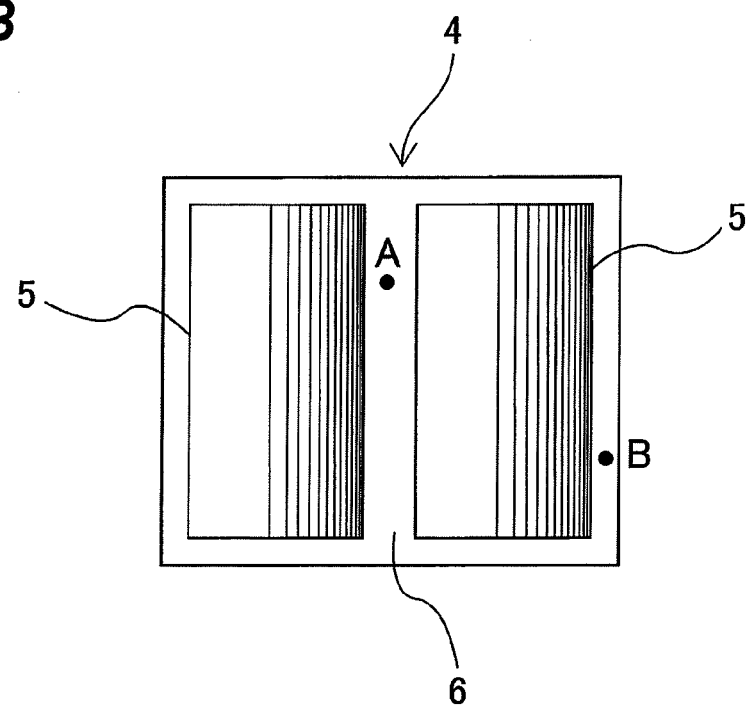
FIG. 2B is a view showing cell regions and a peripheral region that constitute the flash memory.
Figure 4A:
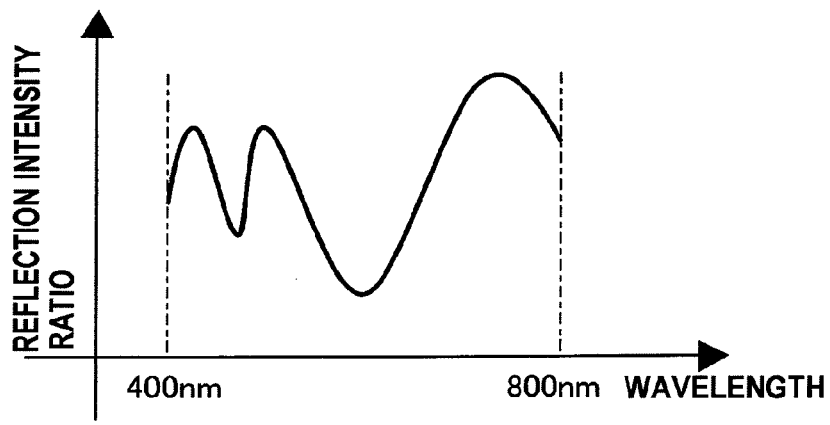
FIG. 4A through FIG. 4C are graphs each showing a spectrum of reflected light.
Figure 4B:
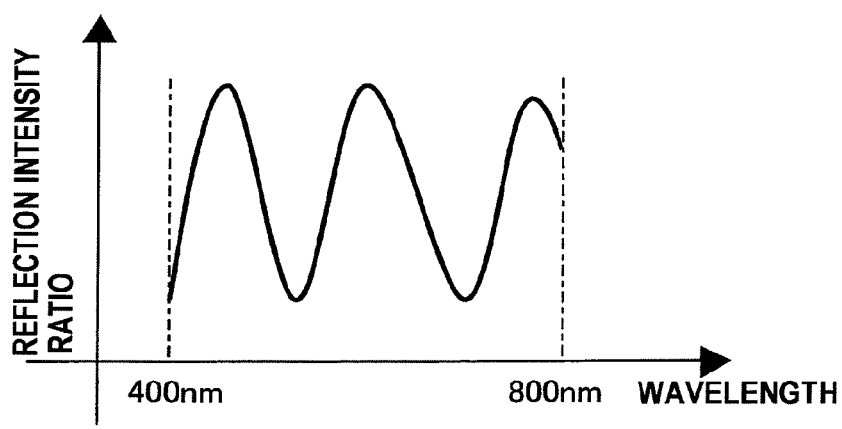
Figure 4C:
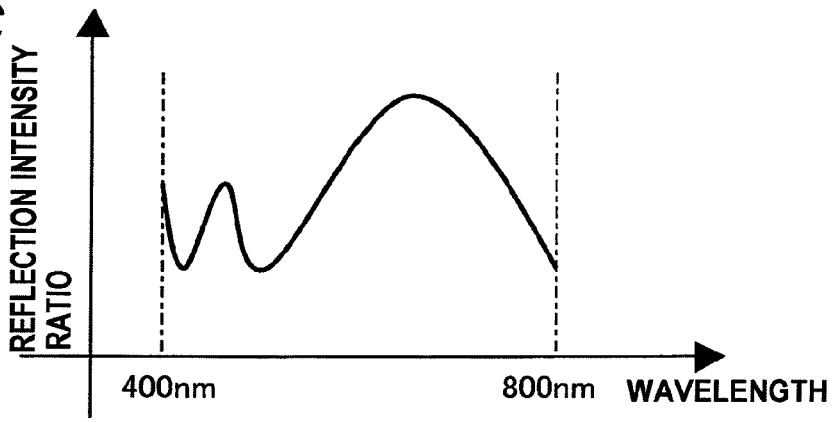

Next, the spectrum of the reflected light obtained during polishing of the substrate shown in FIG. 2A and FIG. 2B will be described. FIG. 4A is a graph showing a spectrum obtained from the reflected light from the cell region 5 shown in FIG. 2B, FIG. 4B is a graph showing a spectrum obtained from the reflected light from a point A in the peripheral region 6 shown in FIG. 2B, and FIG. 4C is a graph showing a spectrum obtained from the reflected light from a point B in the peripheral region 6 shown in FIG. 2B. In FIG. 4A through FIG. 4C, vertical axis represents reflection intensity ratio of the light, and horizontal axis represents wavelength (nm) of the light.

In FIG. 4A through FIG. 4C, the intensity of the light is expressed as reflection intensity ratio. Specifically, the spectrum in FIG. 4A through FIG. 4C shows a relationship between the reflection intensity ratio and the wavelength of the light. The reflection intensity ratio is an index indicating the intensity of the light, and more specifically the reflection intensity ratio is a ratio of a measured intensity of the reflected light and a predetermined reference intensity (i.e., the measured intensity/the reference intensity). The predetermined reference intensity can be an intensity of reflected light obtained when polishing a silicon wafer having no film thereon (i.e., a bare wafer) while supplying pure water onto the polishing pad 22.

The processing device 15 is configured to calculate the above-described reflection intensity ratio from measured value obtained by the spectroscope 13. The reflection intensity ratio varies according to the change in thickness of a film to be polished. This phenomenon is due to interference between light waves. Specifically, the light, directed to the substrate, is reflected off an interface between a medium and the film and an interface between the film and a layer beneath the film. The light waves reflected from these interfaces interfere with each other. The manner of interference between the light waves varies depending on the thickness of the film (i.e., a length of an optical path). Therefore, the intensity of the reflected light from the substrate varies periodically with the thickness of the film. Accordingly, the reflection intensity ratio, which is calculated from the intensity of the reflected light, also varies with the thickness of the film.

Figure 5:
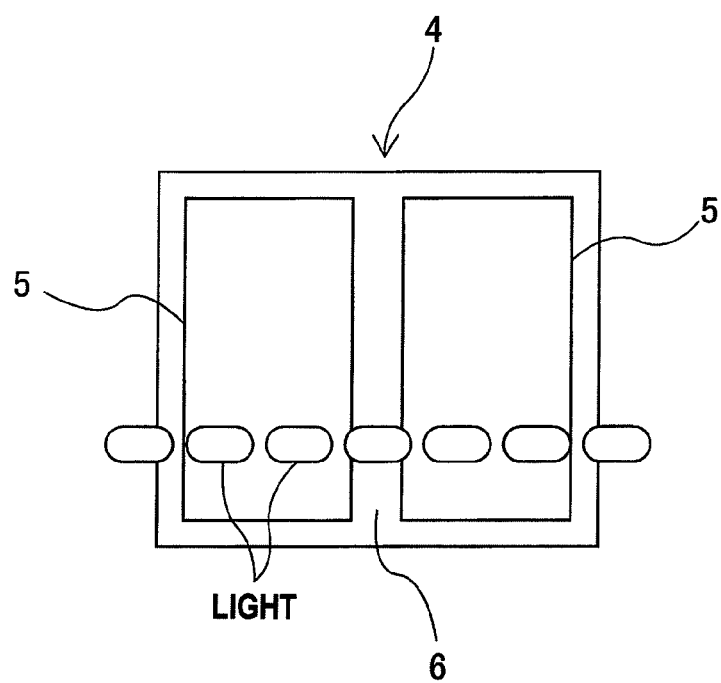
FIG. 5 is a view showing trajectories (or traces) of light applied to a surface of the substrate with rotation of the polishing table.

FIG. 5 is a view showing trajectories of the light applied to the surface of the substrate with rotation of the polishing table. Typically, one flash memory 4 contains two cell regions 5 and a peripheral region 6 surrounding the cell regions 5. An area ratio of the two cell regions 5 to the peripheral region 6 in one flash memory 4 is approximately 7:3. In this embodiment, the light is applied intermittently at short time intervals. Specifically, each time the polishing table 20 makes one revolution, the light is applied to the cell region 5 at least one time, preferably several times. In the example shown in FIG. 5, there are two trajectories of the light (i.e., two exposure spots) in the cell region 5. These exposure spots are measurement points.

The number of measurement points per one cell region 5 depends on a rotational speed of the polishing table 20 and an illumination time per one measurement point, in addition to the size of the cell region 5. For example, in a case where one flash memory 4 shown in FIG. 5 has a size of 12 mm high and 12 mm wide, one cell region 5 has a size of 10 mm high and 5 mm wide, and the rotational speed of the polishing table 20 is 150 revolutions per minute, the illumination time per one measurement point (i.e., measurement time for one measurement point) is about 1.7 milliseconds in order to apply the light to one cell region 5 one time each time the polishing table 20 makes one revolution. Therefore, in order to apply the light to one cell region 5 two times, the illumination time per one measurement point is about 1 millisecond ($\approx 1.7/2$ milliseconds). In this manner, the rotational speed of the polishing table 20 and the illumination time per one measurement point are determined such that at least one measurement point exists in each cell region 5 on the surface of the substrate.

An object to be polished is the cell region 5 that constitutes memory. Therefore, an object to be monitored is the cell region 5. As described above, since the cell region 5 has regular structures, the reflected light from the cell region 5 contains highly reliable film-thickness information. In contrast, the peripheral region 6 has irregular structures, and it is not preferable to use the reflected light from the peripheral region 6 for monitoring polishing of the cell region 5. Thus, the processing device 15 classifies the spectrum created from the reflected light as a spectrum of the reflected light from the cell region 5 or a spectrum of the reflected light from the peripheral region 6, and uses only the spectrum of the reflected light from the cell region 5 for monitoring of polishing.

Since the cell region 5 has the uniform structures in its entirety, substantially the same spectrum is obtained from the reflected light from the cell region 5 regardless of the location of the measurement point. In contrast, as shown in FIG. 4B and FIG. 4C, the spectrum obtained from the reflected light from the peripheral region 6 can vary depending on the location of the measurement point. Spectra that are obtained each time the polishing table 20 makes one revolution contain the spectrum with respect to the cell region 5 and the spectrum with respect to the peripheral region 6. Thus, in this embodiment, the spectrum obtained is classified as the spectrum with respect to the cell region 5 or the spectrum with respect to the peripheral region 6 based on a shape of the spectrum of the reflected light.

The processing device 15 in this embodiment performs the classification of the spectrum using a predetermined classification algorithm. In one example of the classification, the processing device 15 determines a reference spectrum having a shape that most closely matches a shape of the spectrum obtained during polishing. This reference spectrum is determined among a plurality of reference spectra each associated with a film thickness. Then the processing device 15 determines whether or not a film thickness associated with the determined reference spectrum is within a predetermined range. The processing device 15 stores therein in advance the plural reference spectra corresponding to different film thicknesses. The reference spectrum is a theoretical spectrum that is obtained from a simulation of polishing of a substrate having a structure identical to that of the substrate to be polished. That is, the reference spectrum is a spectrum that is to be obtained when a film has a certain thickness. The reference spectra obtained and the corresponding film thicknesses are stored in the processing device 15 in advance.

The processing device 15 calculates a square-sum of difference between the spectrum of the reflected light and each reference spectrum and obtains a plurality of square-sums corresponding to the aforementioned reference spectra. More specifically, each time the spectrum of the reflected light is produced, the processing device 15 calculates the square-sum of differences between measured reflection intensity ratios indicated on the spectrum and theoretical reflection intensity ratios indicated on each reference spectrum. This calculation of the square-sum is repeated with respect to the above-described plural reference spectra, so that the plural square-sums corresponding respectively to these plural reference spectra are obtained. Further, the processing device 15 determines the smallest of the plural square-sums obtained, determines the reference spectrum corresponding to the determined smallest square-sum, and obtains the film thickness associated with the determined reference spectrum. This film thickness obtained is an estimated film thickness associated with the reference spectrum which is the theoretical spectrum.

Figure 6:
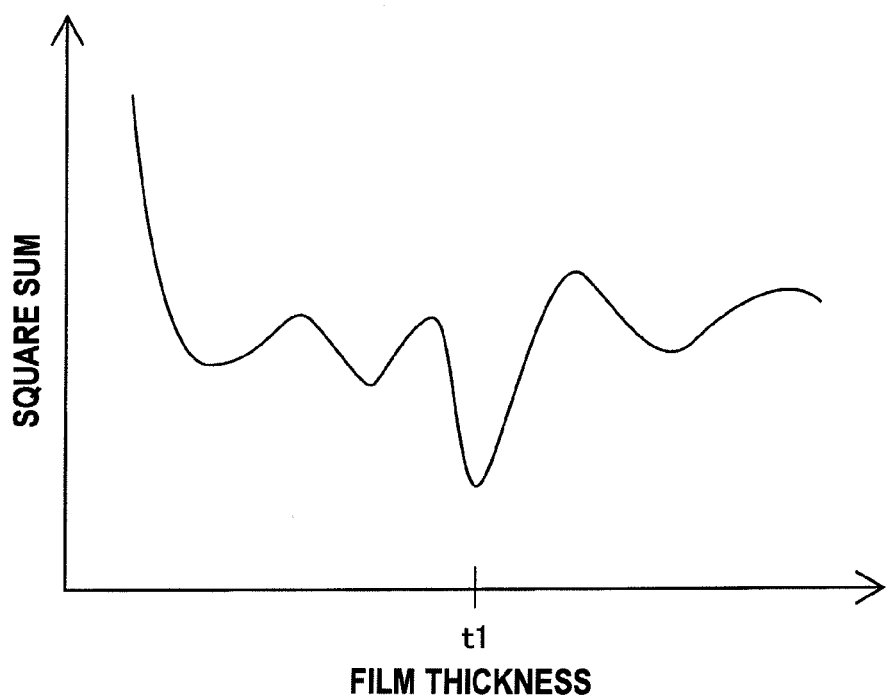
FIG. 6 is a graph having a vertical axis representing square-sum of difference between the spectrum of the reflected light and each reference spectrum and a horizontal axis representing film thickness associated with the reference spectrum.

FIG. 6 is a graph having a vertical axis representing square-sum of the difference between the spectrum of the reflected light and each reference spectrum and a horizontal axis representing film thickness associated with the reference spectrum. In the example shown in FIG. 6, the square-sum takes the minimum at a film thickness t1. From the graph shown in FIG. 6, the spectrum of the reflected light is estimated to be a spectrum obtained when the film thickness is t1. Therefore, the processing device 15 determines that the film thickness corresponding to the spectrum is t1.

Subsequently, the processing device 15 judges whether or not the determined film thickness t1 is within a predetermined reference range. This reference range is defined based on an initial film thickness, a last film thickness, and a polishing time that are actually measured. The reference range is defined on a coordinate system having a coordinate axis representing film thickness and a coordinate axis representing polishing time. The reference range is stored in advance in the processing device 15. The initial film thickness, the last film thickness, and the polishing time are obtained by actually polishing a substrate having an identical structure and by measuring film thickness before and after polishing and a polishing time. Typically, this reference range is registered in a polishing recipe stored in the processing device 15, and remains unchanged regardless of the number of substrates polished. However, when a polishing rate changes greatly due to wear of the polishing pad or other causes, an optimum reference range also changes greatly. Thus, it is preferable that the processing device 15 renew the reference range regularly based on a polishing time of a previously-polished substrate.

Figure 7:
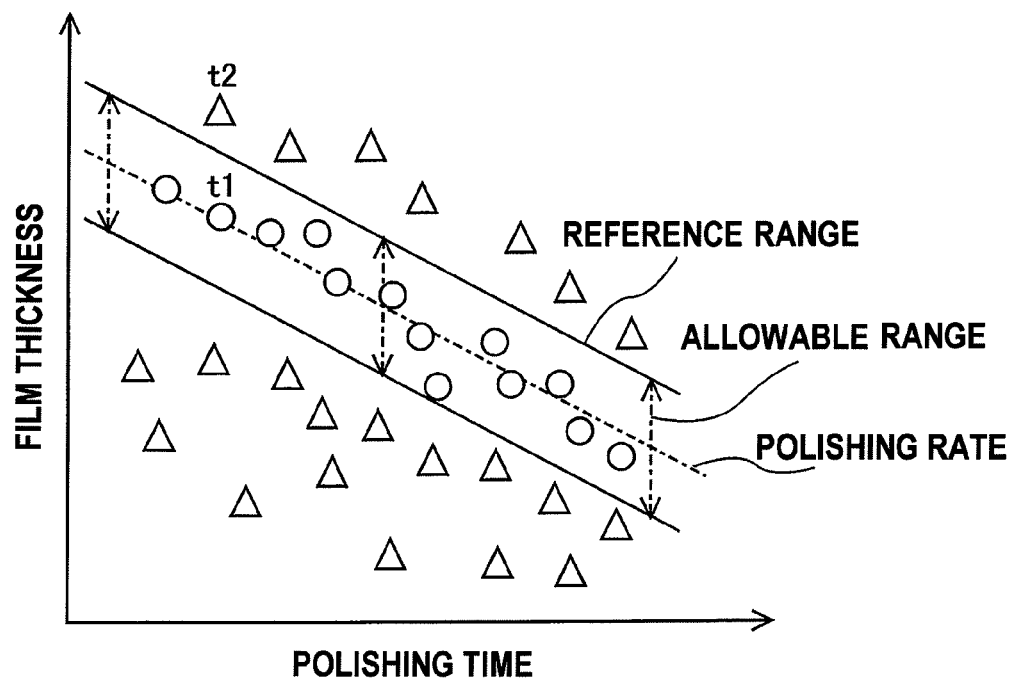
FIG. 7 is a graph showing a reference range of the film thickness.

FIG. 7 is a graph showing the reference range of the film thickness. In FIG. 7, a vertical axis represents film thickness, and a horizontal axis represents polishing time. As shown in FIG. 7, the reference range is determined by a polishing rate (i.e., a removal rate of a film) and an allowable range of the polishing rate. The polishing rate can be calculated from the initial film thickness, the last film thickness, and the polishing time that are obtained by actual measurement. More specifically, the polishing rate is determined by dividing a difference between the initial film thickness and the last film thickness by the polishing time.

When the determined film thickness (estimated film thickness) is within the reference range, the processing device 15 classifies the measured spectrum of the reflected light as a spectrum of the reflected light from the cell region 5. On the other hand, when the determined film thickness is not within the reference range, the processing device 15 classifies the measured spectrum of the reflected light as a spectrum of the reflected light from the peripheral region 6. For example, in FIG. 7, the film thickness t1 falls within the reference range. Therefore, the processing device 15 classifies the measured spectrum as the spectrum of the reflected light from the cell region 5. On the other hand, a film thickness t2 does not fall within the reference range. Therefore, the processing device 15 classifies the measured spectrum as the spectrum of the reflected light from the peripheral region 6.

Further, the processing device 15 monitors the progress of the substrate polishing using the classified spectrum of the reflected light from the cell region 5. Specifically, the processing device 15 calculates a characteristic value S from two reflection intensity ratios corresponding to two wavelengths indicated on the spectrum by using the following equation:

$$S(\lambda 1, \lambda 2) = R(\lambda 1)/[R(\lambda 1) + R(\lambda 2)] \quad (1)$$

where $\lambda 1$ and $\lambda 2$ are wavelength; $R(\lambda 1)$ represents a reflection intensity ratio at the wavelength $\lambda 1$; and $R(\lambda 2)$ represents a reflection intensity ratio at the wavelength $\lambda 2$. The two wavelengths $\lambda 1$ and $\lambda 2$ are selected from the wavelength range of 400 nm to 800 nm that is a measurable range of the spectroscope 13.

Figure 1:
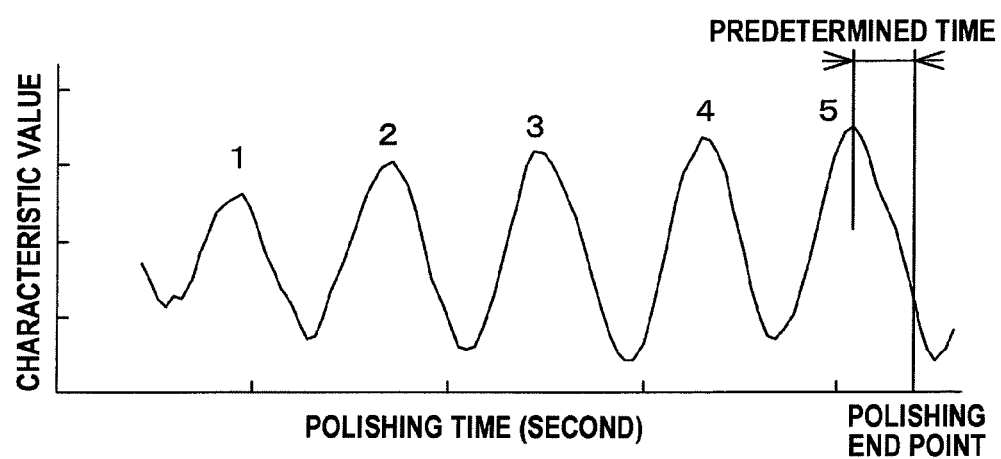
FIG. 1 is a graph showing a manner of change in characteristic value with polishing time.

According to the above equation (1), one reflection intensity ratio is divided by another reflection intensity ratio. Therefore, noises contained in these reflection intensity ratios are cancelled. Therefore, the characteristic value with no noise can be obtained. As shown in FIG. 1, this characteristic value fluctuates periodically with polishing time due to the interference of the light waves. The processing device 15 counts the number of local maximum points or local minimum points of the characteristic value during polishing, determines a time when the number of local maximum points or local minimum points has reached a predetermined value, and determines a polishing end point which is a point of time when a predetermined time has elapsed from the time when the number of local maximum points or local minimum points has reached the predetermined value.

According to the embodiment as described above, the substrate polishing can be monitored accurately using only the spectrum of the reflected light from the cell region 5 having regular structures. Moreover, accurate polishing end point detection can be realized. The number of wavelengths as parameters used in the calculation of the characteristic value is not limited to two. Three or more wavelengths may be used. That is, the characteristic value is calculated from plural reflection intensity ratios at plural wavelengths. When using plural reflection intensity ratios at wavelengths $\lambda 1, \lambda 2, \ldots, \lambda N$, the above-described equation (1) is expressed as $$S(\lambda 1, \lambda 2, \ldots, \lambda N) = R(\lambda 1)/[R(\lambda 1) + R(\lambda 2) + \ldots + R(\lambda N)] \quad (2)$$

Instead of calculating the characteristic value, the estimated film thickness itself (corresponding to the spectrum classified according to the above-described classification algorithm) may be monitored, and the polishing end point may be determined based on the estimated film thickness. The polishing monitoring algorithm using the characteristic value and the polishing monitoring algorithm using the estimated film thickness may be used simultaneously, or may be switched from one to another during polishing. For example, polishing of a first film may be monitored according to the polishing monitoring algorithm using the estimated film thickness, and polishing of a second film underneath the first film may be monitored according to the polishing monitoring algorithm using the characteristic value.

In a case where the peripheral region 6 has regular structures, substrate polishing may be monitored based on the spectrum of the reflected light from the peripheral region 6. In this case, it is possible to use a polishing monitoring algorithm that differs from the polishing monitoring algorithm used in monitoring of polishing based on the spectrum of the reflected light from the cell region 5.

The present invention can be applied to monitoring of the progress of polishing of a substrate having plural regions with different structures formed on the surface thereof. In the above embodiment, the cell region having repeated patterns constitutes a first region and the peripheral region having random patterns constitutes a second region. However, the present invention is not limited to this embodiment. For example, the first region and the second region may be regions having different repeated patterns.

The present invention can also be applied to polishing of a substrate having, in addition to the first region and the second region, a third region formed on a surface thereof. For example, a first reference range for the first region and a second reference range for the second region may be provided as the reference range in FIG. 7. The estimated film thicknesses obtained are classified into an estimated film thickness that belongs to the first reference range, an estimated film thickness that belongs to the second reference range, and an estimated film thickness that belongs to neither the first reference range nor the second reference range, so that the spectra obtained during polishing can be classified into the spectrum of the reflected light from the first region, the spectrum of the reflected light from the second region, and the spectrum of the reflected light from the third region. It is noted that the present invention can be applied to a substrate that further has a fourth region, a fifth region, . . . , n-th region, as well.

It is also possible to monitor substrate polishing based on the spectra of the reflected light from both the first region and the second region. In this case, the spectrum of the reflected light from the first region and the spectrum of the reflected light from the second region may be used simultaneously for monitoring the progress of polishing, or the spectrum to be used may be switched from one to another according to a polishing time or a type of film to be polished. Further, the polishing monitoring algorithm may be changed depending on the spectrum of the reflected light from the first region or the spectrum of the reflected light from the second region.

Depending on the type of substrate, both of the first region and the second region may have regular structures. In such cases, it is preferable to select the region more suitable for monitoring of the progress of polishing. For example, it is preferable to select the region according to a selection criteria, such as an area of region that occupies the surface of the substrate, the ease of polishing of a material that constitutes the region (i.e., the polishing rate), or an interconnect density or minimum pattern width of an underlayer in the region.

The present invention is not limited to polishing of the substrate having flash memories formed thereon, and can be applied to polishing of different types of substrates as well so long as at least two regions with different structures are formed on a surface thereof. For example, the present invention can be applied to polishing of a substrate having DRAM formed thereon.

Further, the classification algorithm executed by the processing device 15 is not limited to the above-described embodiment, and other classification algorithm may be used. For example, the spectrum may be classified based on the number of local maximum points and/or local minimum points that appear on the spectrum of the reflected light.

Specifically, the processing device 15 compares the number of local maximum points and/or local minimum points that appear on the spectrum with a preset reference number, and when the number of local maximum points and/or local minimum points agrees with the reference number, the processing device 15 classifies that spectrum as a spectrum of the reflected light from the cell region 5. On the other hand, when the number of local maximum points and/or local minimum points does not agree with the reference number, the processing device 15 classifies that spectrum as a spectrum of the reflected light from the peripheral region 6. The number of local maximum points and/or local minimum points that appear on the spectrum can vary depending on the change in film thickness of the substrate as a result of polishing. Therefore, it is preferable to provide several reference numbers corresponding to film thickness or polishing time.

The reference number can be determined from the number of local maximum points and/or local minimum points that appear on a theoretical spectrum that is obtained from a simulation of polishing of a substrate having a structure identical to that of the substrate to be polished.

In another example of the classification algorithm, fast Fourier transform (FFT) may be used to classify the spectrum. Specifically, the processing devise 15 decomposes the spectrum as a wave into frequency components by the fast Fourier transform, and compares the frequency components with predetermined reference frequency components. When the frequency components substantially agree with the reference frequency components, the processing devise 15 classifies that spectrum as a spectrum of the reflected light from the cell region 5. When the frequency components do not substantially agree with the reference frequency components, the processing devise 15 classifies that spectrum as a spectrum of the reflected light from the peripheral region 6.

The reference frequency components can be determined by obtaining a theoretical spectrum from a simulation of polishing of a substrate having a structure identical to that of the substrate to be polished and by decomposing the theoretical spectrum into frequency components by the fast Fourier transform.

While the processing device 15 sorts the spectrum according to the programmed classification algorithm, the processing device 15 may classify the spectrum based on the intensity of the reflected light without using the classification algorithm. In some types of substrates, the intensity of the reflected light from the cell region 5 having regular structures is greater than the intensity of the reflected light from the peripheral region 6 having irregular structures. In such cases, when the intensity of the reflected light is not less than a predetermined threshold value, the processing device 15 judges that the reflected light comes from the cell region 5 and classifies the spectrum created from that reflected light as the spectrum of the reflected light from the cell region 5. When the intensity of the reflected light is less than the predetermined threshold value, the processing device 15 judges that the reflected light comes from the peripheral region 6 and classifies the spectrum created from that reflected light as the spectrum of the reflected light from the peripheral region 6. The intensity of the reflected light can be measured by the spectroscope 13. In this example, a polarizing filter for reducing only the reflected light from the peripheral region 6 may be provided between the substrate and the light-receiving unit 12 or between the light-receiving unit 12 and the spectroscope 13.

Figure 8:
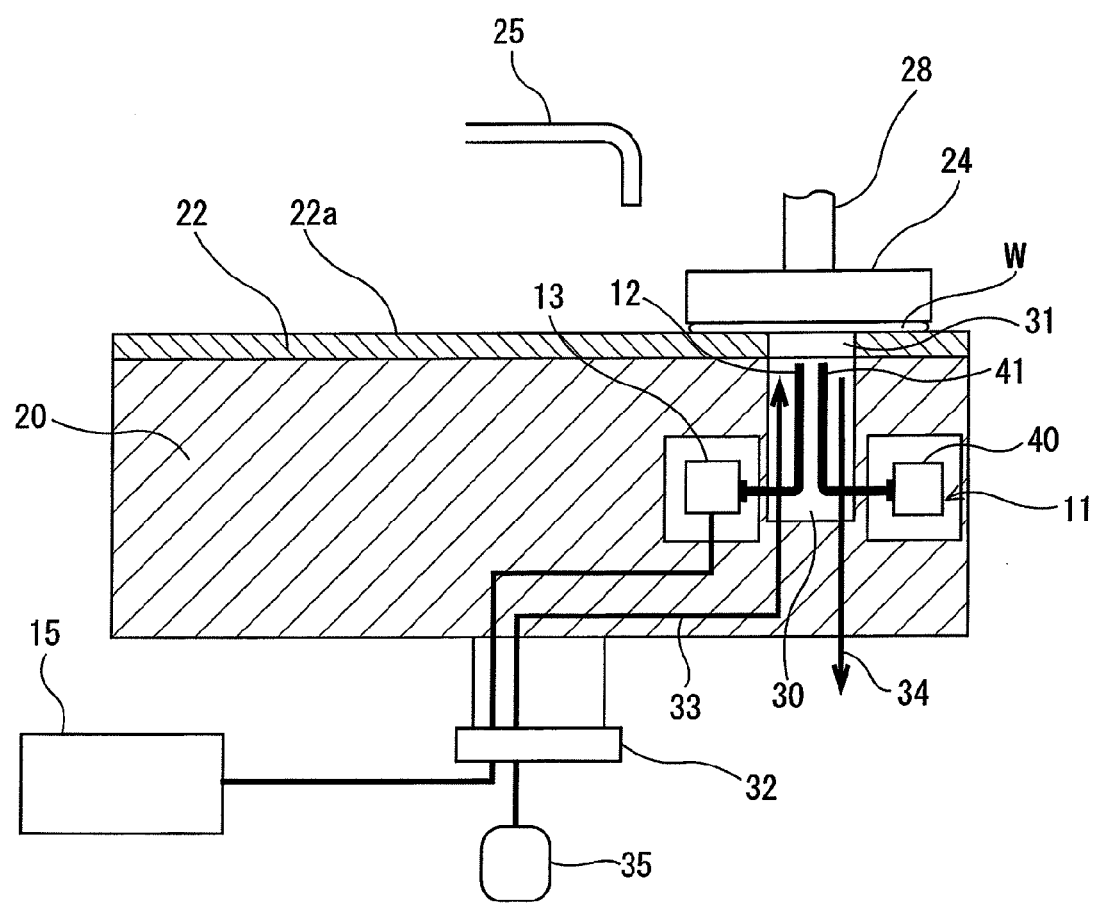
FIG. 8 is a cross-sectional view schematically showing a polishing apparatus having a polishing monitoring device capable of performing the polishing monitoring method according the embodiment of the present invention.

FIG. 8 is a cross-sectional view schematically showing a polishing apparatus having the polishing monitoring device capable of performing the polishing monitoring method according the embodiment of the present invention as described above. As shown in FIG. 8, the polishing apparatus includes the polishing table 20 for supporting the polishing pad 22 thereon, a top ring 24 configured to hold a substrate W and to press the substrate W against the polishing pad 22, and a polishing liquid supply mechanism 25 configured to supply a polishing liquid (slurry) onto the polishing pad 22. The polishing table 20 is coupled to a motor (not shown in the drawing) provided below the polishing table 20, so that the polishing table 20 can be rotated about its own axis. The polishing pad 22 is secured to an upper surface of the polishing table 20.

The polishing pad 22 has an upper surface 22a, which provides a polishing surface for polishing the substrate W. The top ring 24 is coupled to a motor and an elevating cylinder (not shown in the drawing) via a top ring shaft 28. This configuration allows the top ring 24 to move vertically and to rotate about the top ring shaft 28. The top ring 24 has a lower surface which is configured to hold the substrate W by a vacuum suction or the like.

The substrate W, held on the lower surface of the top ring 24, is rotated by the top ring 24, and is pressed by the top ring 24 against the polishing pad 22 on the rotating polishing table 20. During the sliding contact between the substrate W and the polishing pad 22, the polishing liquid is supplied onto the polishing surface 22a of the polishing pad 22 from the polishing liquid supply mechanism 25. The surface of the substrate W is polished in the presence of the polishing liquid between the surface of the substrate W and the polishing pad 22. A relative movement mechanism for providing the sliding contact between the substrate W and the polishing pad 22 is constructed by the polishing table 20 and the top ring 24.

The polishing table 20 has a hole 30 whose upper end lies in the upper surface of the polishing table 20. The polishing pad 22 has a through-hole 31 at a position corresponding to the hole 30. The hole 30 and the through-hole 31 are in fluid communication with each other. An upper end of the through-hole 31 lies in the polishing surface 22a. The hole 30 is coupled to a liquid supply source 35 via a liquid supply passage 33 and a rotary joint 32. During polishing, the liquid supply source 35 supplies water (preferably pure water) as a transparent liquid into the hole 30. The water fills a space formed by the lower surface of the substrate W and the through-hole 31, and is expelled therefrom through a liquid discharge passage 34. The polishing liquid is discharged with the water and thus a path of the light is secured. The liquid supply passage 33 is provided with a valve (not shown in the drawing) configured to operate in conjunction with the rotation of the polishing table 20. The valve operates so as to stop the flow of the water or reduce the flow of the water when the substrate W is not located above the through-hole 31.

The polishing apparatus has the polishing monitoring device for monitoring the progress of polishing and detecting the polishing end point according to the above-described method. The polishing monitoring device includes the light-applying unit 11 configured to direct the light to the surface, to be polished, of the substrate W, optical fiber 12 as the light-receiving unit configured to receive the reflected light returning from the substrate W, the spectroscope 13 configured to decompose the reflected light according to the wavelength and to measure the intensity of the reflected light throughout the predetermined wavelength range, and the processing device 15 configured to produce the spectrum from the measurement data obtained by the spectroscope 13 and to monitor the progress of polishing of the substrate based on the change in the spectrum. The spectrum indicates the light intensity distributed over the predetermined wavelength range.

The light-applying unit 11 includes a light source 40 and an optical fiber 41 coupled to the light source 40. The optical fiber 41 is a light-transmitting element for directing the light of the light source 40 to the surface of the substrate W. The optical fiber 41 extends in the hole 30 from the light source 40 to a position near the surface of the substrate W to be polished. The optical fiber 41 and the optical fiber 12 have tip ends, respectively, facing the center of the substrate W held by the top ring 24, so that the light is applied to regions including the center of the substrate W each time the polishing table 20 rotates, as shown in FIG. 3B.

The light source 40 is configured to apply the light to the substrate W intermittently at predetermined time intervals. A light emitting diode (LED), a halogen lamp, a xenon flash lamp, or the like can be used as the light source 40 for emitting multiwavelength light. The optical fiber 41 and the optical fiber 12 are arranged in parallel with each other. The tip ends of the optical fiber 41 and the optical fiber 12 are arranged so as to face in a direction substantially perpendicular to the surface of the substrate W, so that the optical fiber 41 directs the light to the surface of the substrate W in substantially the perpendicular direction.

During polishing of the substrate W, the light-applying unit 11 applies the light to the substrate W intermittently, and the optical fiber 12 receives the reflected light from the substrate W. During the application of the light, the hole 30 is supplied with the water, whereby the space between the tip ends of the optical fibers 41 and 12 and the surface of the substrate W is filled with the water. The spectroscope 13 measures the intensity of the reflected light at each wavelength, and the processing device 15 produces the spectrum that indicates the relationship between the reflection intensity ratio and the wavelength. Further, the processing device 15 classifies the spectrum as the spectrum of the reflected light from the cell region 5 or as the spectrum of the reflected light from the peripheral region 6. The processing device 15 calculates the characteristic value which is a polishing index indicating the progress of polishing, monitors the progress of the polishing and determines the polishing end point based on the change in the characteristic value with time.

Figure 9:
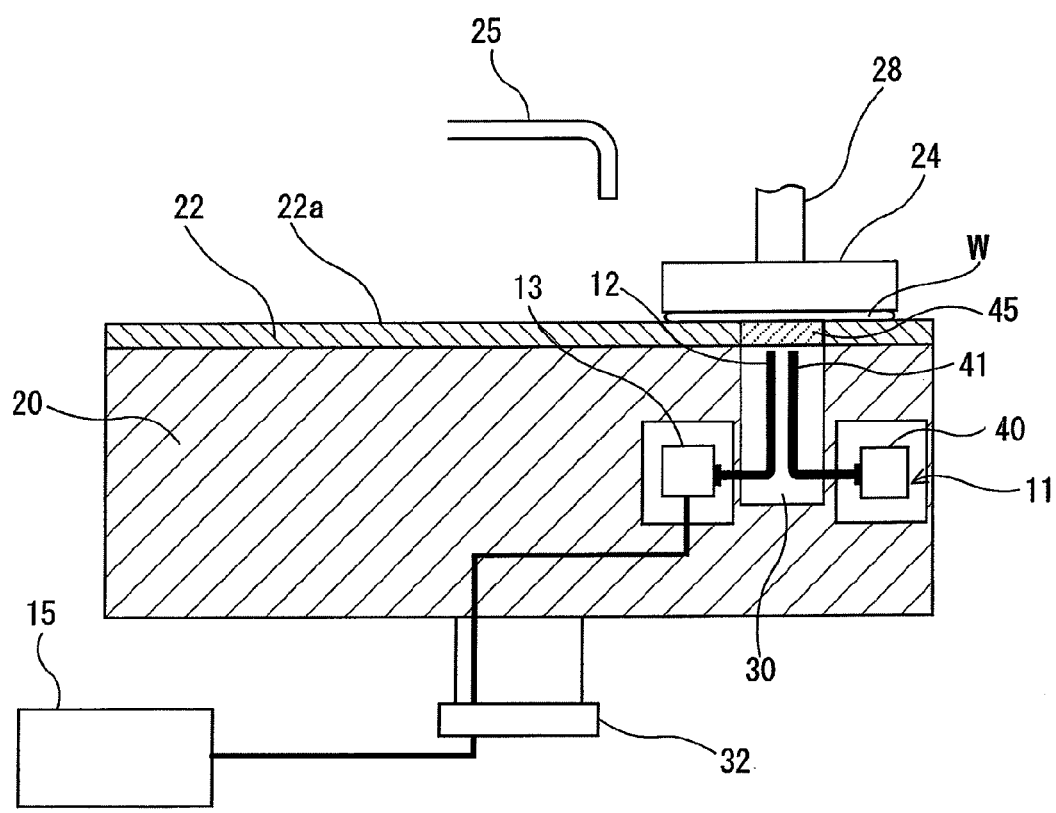
FIG. 9 is a cross-sectional view showing a modified example of the polishing apparatus shown in FIG. 8.

FIG. 9 is a cross-sectional view showing a modified example of the polishing apparatus shown in FIG. 8. In the example shown in FIG. 9, the liquid supply passage, the liquid discharge passage, and the liquid supply source are not provided. Instead, a transparent window 45 is provided in the polishing pad 22. The optical fiber 41 of the light-applying unit 11 directs the light through the transparent window 45 to the surface of the substrate W on the polishing pad 22, and the optical fiber 12 as the light-receiving unit receives the reflected light from the substrate W through the transparent window 45. The other structures are the same as those of the polishing apparatus shown in FIG. 8.

Figure 10:
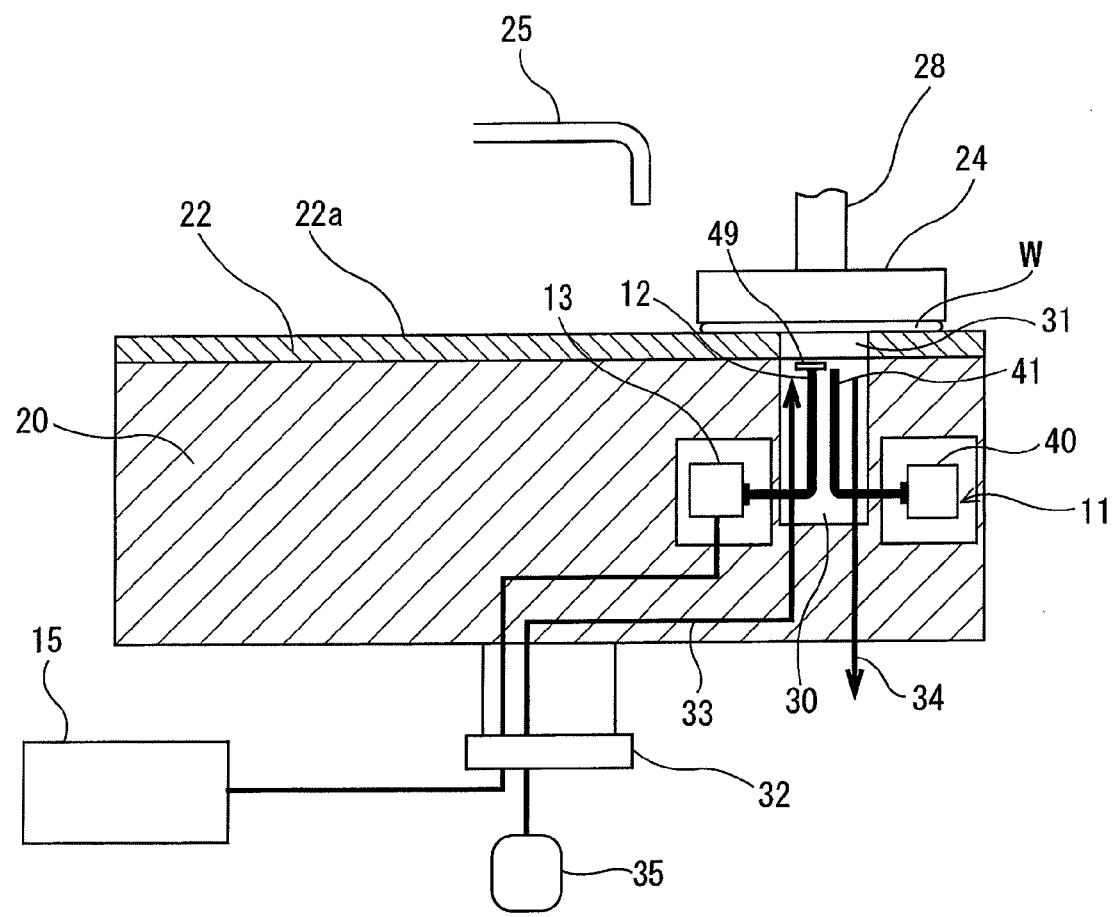
FIG. 10 is a cross-sectional view showing another modified example of the polishing apparatus shown in FIG. 8.

FIG. 10 is a cross-sectional view showing another modified example of the polishing apparatus shown in FIG. 8. In this example, the aforementioned polarizing filter 49 is disposed between the optical fiber 12 as the light-receiving unit and the substrate W. This polarizing filter 49 has a function of reducing only the reflected light from the peripheral region 6 on the surface of the substrate W. While the reflected light from the cell region 5 passes through the polarizing filter 49 to reach the spectroscope 13, the reflected light from the peripheral region 6 is reduced by the polarizing filter 49. This results in a great difference in intensity (or quantity of light) between the reflected light from the cell region 5 and the reflected light from the peripheral region 6. Therefore, the processing device 15 can classify the spectrum according to the intensity of the reflected light that returns from the substrate W.

The polarizing filter 49 may be disposed between the optical fiber 12 and the spectroscope 13. In this case, a polarization maintaining fiber is used as the optical fiber 12. Although the polarization maintaining fiber has a low degree of polarization, it may be able to obtain the same result as the polarizing filter with no polarizing filter.

Figure 11:
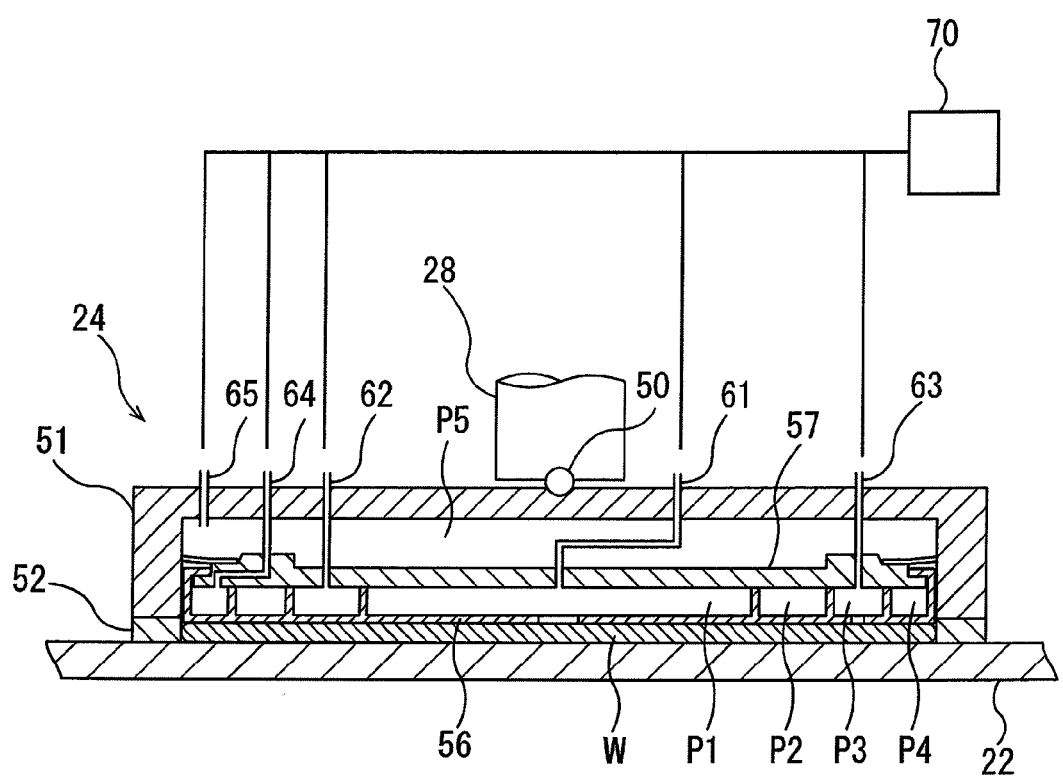
FIG. 11 is a cross-sectional view showing an example of a top ring having multiple pressing mechanisms for independently pressing multiple zones of the substrate.

FIG. 11 is a cross-sectional view showing an example of the top ring having multiple pressing mechanisms for pressing plural zones of the substrate independently. The top ring 24 has a top ring body 51 coupled to a top ring shaft 28 via a flexible joint 50, and a retainer ring 52 provided on a lower portion of the top ring body 51. The top ring 24 further has a circular flexible membrane 56 to be brought into contact with the substrate W and a chucking plate 57 that holds the flexible membrane 56. The flexible membrane 56 and the chucking plate 57 are disposed beneath the top ring body 51. Four pressure chambers (air bags) P1, P2, P3, and P4 are provided between the flexible membrane 56 and the chucking plate 57. The pressure chambers P1, P2, P3, and P4 are formed by the flexible membrane 56 and the chucking plate 57. The central pressure chamber P1 has a circular shape, and the other pressure chambers P2, P3, and P4 have an annular shape. These pressure chambers P1, P2, P3, and P4 are in a concentric arrangement.

Pressurized fluid (e.g., pressurized air) is supplied into the pressure chambers P1, P2, P3, and P4 or vacuum is developed in the pressure chambers P1, P2, P3, and P4 by a pressure-adjusting device 70 via fluid passages 61, 62, 63, and 64, respectively. The internal pressures of the pressure chambers P1, P2, P3, and P4 can be changed independently to thereby independently adjust pressing forces applied to four zones of the substrate W: a central zone, an inner middle zone, an outer middle zone, and a peripheral zone. Further, by elevating or lowering the top ring 24 in its entirety, the retainer ring 52 can press the polishing pad 22 at a predetermined pressing force.

A pressure chamber P5 is formed between the chucking plate 57 and the top ring body 51. Pressurized fluid is supplied into the pressure chamber P5 or vacuum is developed in the pressure chamber P5 by the pressure-adjusting device 70 via a fluid passage 65. With this operation, the chucking plate 57 and the flexible membrane 56 in their entirety can be moved up and down. The retainer ring 52 is arranged around the substrate W so as to prevent the substrate W from coming off the top ring 24 during polishing. The flexible membrane 56 has an opening in a portion that forms the pressure chamber P3, so that the substrate W can be held by the top ring 24 via the vacuum suction by producing vacuum in the pressure chamber P3. Further, the substrate W can be released from the top ring 24 by supplying nitrogen gas or clean air into the pressure chamber P3.

The processing device 15 determines target values of the internal pressures in the respective pressure chambers P1, P2, P3, and P4 based on the progress of polishing at the measurement points in corresponding locations of the pressure chambers P1, P2, P3, and P4. The processing device 15 sends command signals to the pressure-adjusting device 70 to control the pressure-adjusting device 70 such that the internal pressures of the pressure chambers P1, P2, P3, and P4 agree with the target values. Because the top ring 24 has the multiple pressure chambers, it can press the multiple zones of the surface of the substrate independently according to the progress of polishing. Therefore, the film can be polished uniformly.

The previous description of embodiments is provided to enable a person skilled in the art to make and use the present invention. Moreover, various modifications to these embodiments will be readily apparent to those skilled in the art, and the generic principles and specific examples defined herein may be applied to other embodiments. Therefore, the present invention is not intended to be limited to the embodiments described herein but is to be accorded the widest scope as defined by limitation of the claims and equivalents.

What is claimed is:

1. A method of monitoring progress of polishing of a substrate having on a surface thereof at least two regions including a first region and a second region with different structures, said method comprising:
    polishing the substrate by pressing the substrate against a polishing pad on a rotating polishing table;
    during said polishing of the substrate, applying light to plural measurement points on the substrate;
    receiving reflected light from each measurement point;
    measuring intensity of the reflected light throughout a predetermined wavelength range;
    producing a spectrum of the reflected light from measurement values of the intensity;
    classifying the spectrum as spectrum of the reflected light from the first region or as spectrum of the reflected light from the second region based on a shape of the spectrum or the intensity of the reflected light; and
    monitoring the progress of polishing of the substrate based on a temporal change in the spectrum of the reflected light from the first region,
    wherein said classifying of the spectrum comprises:
    classifying the spectrum as a spectrum of the reflected light from the first region when the number of local maximum points and/or local minimum points that appear on the spectrum agrees with a predetermined reference number; and
    classifying the spectrum as a spectrum of the reflected light from the second region when the number of local maximum points and/or local minimum points that appear on the spectrum does not agree with the predetermined reference number.

2. The method according to claim 1, further comprising:
    further monitoring the progress of polishing of the substrate based on a temporal change in the spectrum of the reflected light from the second region.

3. The method according to claim 2, wherein said monitoring of the progress of polishing of the substrate based on the temporal change in the spectrum of the reflected light from the first region and said monitoring of the progress of polishing of the substrate based on the temporal change in the spectrum of the reflected light from the second region are performed simultaneously or successively.

4. The method according to claim 2, wherein said monitoring of the progress of polishing of the substrate based on the temporal change in the spectrum of the reflected light from the first region and said monitoring of the progress of polishing of the substrate based on the temporal change in the spectrum of the reflected light from the second region are performed according to different polishing monitoring algorithms.

5. The method according to claim 1, wherein said monitoring of the progress of polishing of the substrate is performed according to at least two polishing monitoring algorithms, which are switched from one to another during polishing.

6. The method according to claim 1, wherein said classifying of the spectrum comprises:
    calculating a square-sum of difference between the spectrum and a reference spectrum selected from plural reference spectra each associated with a film thickness;
    repeating said calculating of the square-sum to obtain plural square-sums corresponding to the plural reference spectra;
    determining a reference spectrum corresponding to a smallest of the plural square-sums to obtain a film thickness associated with the determined reference spectrum;
    classifying the spectrum as a spectrum of the reflected light from the first region when the film thickness obtained is within a predetermined reference range; and
    classifying the spectrum as a spectrum of the reflected light from the second region when the film thickness obtained is not within the predetermined reference range.

7. The method according to claim 1, wherein said classifying of the spectrum comprises:
    decomposing the spectrum into frequency components by fast Fourier transform;
    classifying the spectrum as a spectrum of the reflected light from the first region when the frequency components substantially agree with predetermined reference frequency components; and
    classifying the spectrum as a spectrum of the reflected light from the second region when the frequency components do not substantially agree with the predetermined reference frequency components.

8. The method according to claim 1, wherein said classifying of the spectrum comprises:
    comparing the intensity of the reflected light with a predetermined threshold value;
    classifying the spectrum as a spectrum of the reflected light from the first region when the intensity of the reflected light is not less than the predetermined threshold value; and
    classifying the spectrum as a spectrum of the reflected light from the second region when the intensity of the reflected light is less than the predetermined threshold value.

9. The method according to claim 1, further comprising:
    determining a polishing end point of the substrate based on the temporal change in the spectrum of the reflected light from the first region.

10. The method according to claim 1, wherein:
    the substrate has memories formed on the surface thereof;
    the first region is a cell region of each memory; and
    the second region is a peripheral region surrounding the cell region.

11. The method according to claim 1, wherein the first region has regular structures and the second region has irregular structures.

12. An apparatus for polishing a substrate having on a surface thereof at least two regions including a first region and a second region with different structures, said apparatus comprising:
    a rotatable polishing table for supporting a polishing pad thereon;
    a top ring configured to press the substrate against the polishing pad;
    a light-applying unit configured to apply light to plural measurement points on the substrate;
    a light-receiving unit configured to receive reflected light from each measurement point;
    a spectroscope configured to measure intensity of the reflected light throughout a predetermined wavelength range; and a processing device configured to produce a spectrum of the reflected light from measurement values of the intensity, wherein said processing device is configured to classify the spectrum as spectrum of the reflected light from the first region or as spectrum of the reflected light from the second region based on a shape of the spectrum or the intensity of the reflected light, and monitor the progress of polishing of the substrate based on a temporal change in the spectrum of the reflected light from the first region, wherein said processing device performs classifying of the spectrum by:

classifying the spectrum as a spectrum of the reflected light from the first region when the number of local maximum points and/or local minimum points that appear on the spectrum agrees with a predetermined reference number; and classifying the spectrum as a spectrum of the reflected light from the second region when the number of local maximum points and/or local minimum points that appear on the spectrum does not agree with the predetermined reference number.

13. The apparatus according to claim 12, wherein said processing device is configured to further monitor the progress of polishing of the substrate based on a temporal change in the spectrum of the reflected light from the second region.

14. The apparatus according to claim 13, wherein said processing device performs monitoring of the progress of polishing of the substrate based on the temporal change in the spectrum of the reflected light from the first region and monitoring of the progress of polishing of the substrate based on the temporal change in the spectrum of the reflected light from the second region simultaneously or successively.

15. The apparatus according to claim 13, wherein said processing device performs monitoring of the progress of polishing of the substrate based on the temporal change in the spectrum of the reflected light from the first region and monitoring of the progress of polishing of the substrate based on the temporal change in the spectrum of the reflected light from the second region according to different polishing monitoring algorithms.

16. The apparatus according to claim 12, wherein said processing device performs monitoring of the progress of polishing of the substrate according to at least two polishing monitoring algorithms, which are switched from one to another during polishing.

17. The apparatus according to claim 12, wherein said processing device performs classifying of the spectrum by:

calculating a square-sum of difference between the spectrum and a reference spectrum selected from plural reference spectra each associated with a film thickness;

repeating said calculating of the square-sum to obtain plural square-sums corresponding to the plural reference spectra;

determining a reference spectrum corresponding to a smallest of the plural square-sums to obtain a film thickness associated with the determined reference spectrum;

classifying the spectrum as a spectrum of the reflected light from the first region when the film thickness obtained is within a predetermined reference range; and classifying the spectrum as a spectrum of the reflected light from the second region when the film thickness obtained is not within the predetermined reference range.

18. The apparatus according to claim 12, wherein said processing device performs classifying of the spectrum by:

decomposing the spectrum into frequency components by fast Fourier transform;

classifying the spectrum as a spectrum of the reflected light from the first region when the frequency components substantially agree with predetermined reference frequency components; and classifying the spectrum as a spectrum of the reflected light from the second region when the frequency components do not substantially agree with the predetermined reference frequency components.

19. The apparatus according to claim 12, wherein said processing device performs classifying of the spectrum by:

comparing the intensity of the reflected light with a predetermined threshold value;

classifying the spectrum as a spectrum of the reflected light from the first region when the intensity of the reflected light is not less than the predetermined threshold value; and classifying the spectrum as a spectrum of the reflected light from the second region when the intensity of the reflected light is less than the predetermined threshold value.

20. The apparatus according to claim 12, wherein said processing device is further configured to determine a polishing end point of the substrate based on the temporal change in the spectrum of the reflected light from the first region.

21. The apparatus according to claim 12, wherein:

the substrate has memories formed on the surface thereof;

the first region is a cell region of each memory; and the second region is a peripheral region surrounding the cell region.

22. The apparatus according to claim 12, wherein the first region has regular structures and the second region has irregular structures.

23. The apparatus according to claim 12, wherein said top ring has multiple pressing mechanisms capable of pressing multiple zones of the substrate independently.

* * * * *